(12) United States Patent
Al-Ali

(10) Patent No.: US 6,760,607 B2
(45) Date of Patent: Jul. 6, 2004

(54) RIBBON CABLE SUBSTRATE PULSE OXIMETRY SENSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 10/032,339

(22) Filed: Dec. 20, 2001

(65) Prior Publication Data

US 2002/0095074 A1 Jul. 18, 2002

Related U.S. Application Data

(60) Provisional application No. 60/258,859, filed on Dec. 29, 2000.

(51) Int. Cl.[7] .................................................. A61B 5/00
(52) U.S. Cl. ...................................................... 600/322
(58) Field of Search ................................ 600/310, 322, 600/323

(56) References Cited

U.S. PATENT DOCUMENTS

| | | | |
|---|---|---|---|
| 4,964,408 A | | 10/1990 | Hink et al. |
| 5,054,488 A | | 10/1991 | Muz |
| 5,069,213 A | * | 12/1991 | Polczynski .................. 600/323 |
| 5,758,644 A | | 6/1998 | Diab et al. |
| 5,782,757 A | | 7/1998 | Diab et al. |
| 5,906,503 A | * | 5/1999 | Wiencek et al. ............ 439/418 |

FOREIGN PATENT DOCUMENTS

DE 33 05 246 C1 10/1984
EP 0438 276 A1 1/1991

OTHER PUBLICATIONS

U.S. patent application No. 09/456,666.

* cited by examiner

*Primary Examiner*—Eric F. Winakur
*Assistant Examiner*—David J. McCrosky
(74) *Attorney, Agent, or Firm*—Knobbe, Martens, Olson & Bear, LLP

(57) ABSTRACT

A pulse oximetry sensor is constructed using ribbon cable as a substrate for component mounting and interconnection as well as for forming a patient cable connector. The ribbon cable is constructed of multiple conductors spaced apart within an insulation layer and is advantageously cut to length to form a substrate for a particular type of sensor, such as a neonatal, pediatric or adult sensor. A detector is attached to a pair of conductors at a component end of the substrate, after insulation is stripped from the conductor tips. Another pair of conductors is cut to a length between the substrate ends. An emitter is attached to the shortened conductors after insulation is stripped from the conductor tips. Insulation is also stripped from the conductor tips at a connector end of the substrate. Pins are attached to each of these tips, and the pins are used to form a patient cable connector. The assembled substrate is mounted to an adhesive tape that is configured to removably attach the sensor to a patient so that the emitter transmits light into a tissue portion of the patient and the detector correspondingly receives emitted light that is not absorbed by the tissue. The ribbon cable may have one or more conductive layers with embedded conductors for electrical noise shielding, particularly at the detector.

11 Claims, 17 Drawing Sheets

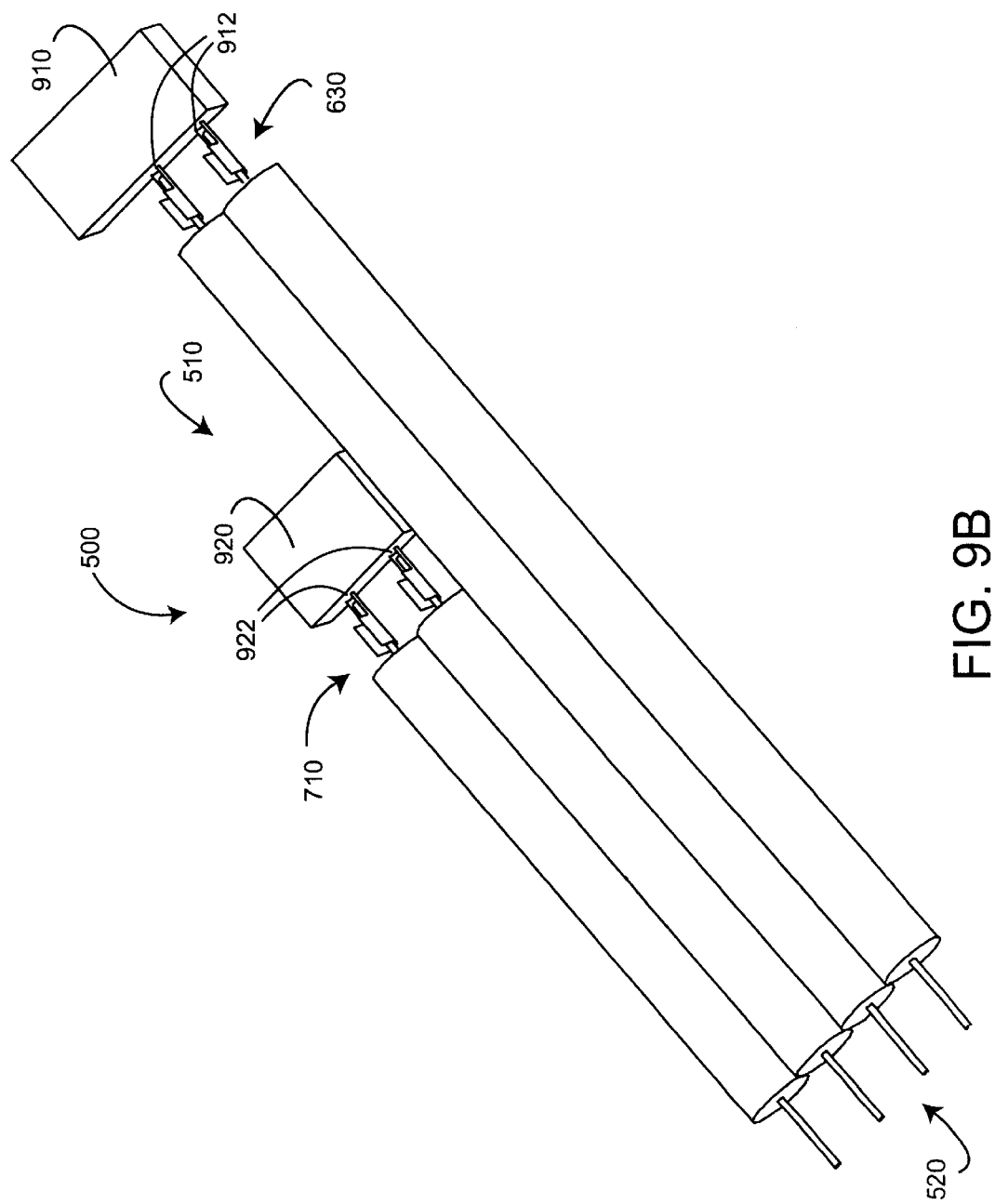

RIBBON CABLE SUBSTRATE PULSE OXIMETRY SENSOR

REFERENCE TO RELATED APPLICATION

The present application claims priority benefit under 35 U.S.C. § 119(e) from U.S. Provisional Application No. 60/258,859, filed Dec. 29, 2000, entitled "RIBBON CABLE SUBSTRATE PULSE OXIMETRY SENSOR." The present application incorporates the foregoing application herein by reference.

BACKGROUND OF THE INVENTION

Description of the Related Art

Pulse oximetry is a widely accepted noninvasive procedure for measuring the oxygen saturation level of arterial blood, an indicator of a person's oxygen supply. Early detection of low blood oxygen level is critical in the medical field, for example in critical care and surgical applications, because an insufficient supply of oxygen can result in brain damage and death in a matter of minutes. A pulse oximetry system includes a sensor applied to a patient, a pulse oximeter, and a patient cable connecting the sensor and the pulse oximeter. The pulse oximeter may be a standalone device or may be incorporated as a module or built-in portion of a multiparameter patient monitoring system and typically provides a numerical readout of the patient's oxygen saturation, a numerical readout of pulse rate, and an audible indicator or "beep" that occurs in response to each pulse. In addition, the pulse oximeter may display the patient's plethysmograph, which provides a visual display of the patient's pulse contour and pulse rate.

SUMMARY OF THE INVENTION

FIGS. 1 and 2 illustrate one type of circuit configuration for a pulse oximetry sensor, such as described in U.S. Pat. No. 5,782,757 entitled "Low Noise Optical Probe," which is assigned to the assignee of the present application, and is incorporated herein by reference. As shown in FIG. 1, a sensor 100 that can be attached, for example, to an adult patient's finger or an infant patient's foot, has both red and infrared LEDs 110 and a photodiode detector 120. For finger attachment, the sensor is configured so that the LEDs 110 project light through the fingernail and into the blood vessels and capillaries underneath. The photodiode 120 is positioned at the finger tip opposite the fingernail so as to detect the LED emitted light as it emerges from the finger tissues. The sensor 100 may have an identification (ID) element, such as a resistor 130 with multiple uses depending on the manufacturer, such as an indicator of LED wavelength, sensor type or manufacturer. LED pinouts 140 connect the LEDs 110 to LED drivers in a pulse oximetry monitor (not shown) via a patient cable (not shown). Detector pinouts 150 connect the detector 120 to front end signal conditioning and analog-to-digital conversion within the monitor, also via the patient cable.

As shown in FIG. 2, a sensor circuit may comprise a flexible circuit substrate 200 having printed traces 204 of deposited or etched conductive material, including connector traces 206. Mounted on the substrate 200 and soldered to the traces 204 so as to create an electrical connection are an LED component 210 having both red and infrared LEDs 110 (FIG. 1) encapsulated on a leaded carrier, a detector component 220 having a photodiode 120 (FIG. 1) encapsulated on a leaded carrier and an ID element 230 such as a resistor 130 (FIG. 1) on a leadless carrier. The connector traces 206 have detector pinouts 140, LED pinouts 150 and shielding pinouts 260 for noise suppression.

A ribbon cable substrate pulse oximetry sensor utilizes a ribbon cable to physically mount and electrically connect the sensor components. A ribbon cable substrate has several advantages over a flexible circuit or similar substrate for manufacturing a pulse oximetry sensor. Ribbon cable can be purchased "off-the-shelf" in bulk quantities, such as on large spools, as compared with flexible circuits, which are custom manufactured. Further, unlike flexible circuits that must be manufactured in various sizes for various sensor types, ribbon cable can be cut-to-length as required. In additional, as described below, ribbon cable is amenable to automated manufacturing techniques. Thus, use of ribbon cable as a sensor substrate can significantly reduce sensor costs as well as simplify the manufacturing process.

One aspect of a physiological sensor comprises a ribbon cable having a plurality of conductors extending within an insulation layer between a first end and a second end. A detector is mounted to the ribbon cable and electrically connected to at least a first pair of the conductors. An emitter is also mounted to the ribbon cable and electrically connected to at least a second pair of the conductors. At least one of the detector and the emitter are mounted at the first end of the ribbon cable, and a connector is mounted to the ribbon cable at the second end. A retainer is mounted to the ribbon cable and configured to removably attach the ribbon cable to tissue so that the emitter may transmit light into a tissue sample and the detector may receive light from the tissue sample.

In one embodiment, the detector is mounted to the ribbon cable at the first end and the emitter is mounted to the ribbon cable between the first and second ends. In this manner, the ribbon cable can be folded around a tissue portion of a patient so that the emitter opposes the detector on either side of the tissue portion. In another embodiment, the connector comprises a plurality of pins each enclosing one of a plurality of end portions of the conductors, where the insulation is stripped from the end portions at the second end. An encapsulant is disposed around a portion of the pins and the second end so as to form a housing portion of the connector. Alternatively, a welded connector shell is disposed around a portion of the pins and the second end so as to form a housing portion of the connector.

In a further embodiment, the ribbon cable comprises a first conductive layer shielding the first pair of conductors, where the first conductive layer has a first embedded conductor extending to the connector. A detector shield may be disposed around the detector and electrically connected to the first embedded conductor. Also, there may be a second conductive layer shielding the first pair and the second pair of conductors, where the second conductive layer has a second embedded conductor extending to the connector.

Another aspect of a physiological sensor is a manufacturing method comprising the step of cutting a substrate from a length of ribbon cable having a plurality of conductors to form a connector end and a component end of the substrate. The length of the substrate is measured to conform to a particular sensor type. Further steps are stripping a first portion of insulation from the component end to expose a detector contact portion of the conductors and stripping a second portion of insulation from the component end to expose an emitter contact portion of the conductors. Additional steps are attaching a detector and an emitter at the component end so that a plurality of detector leads of the detector are electrically connected to the detector contact portion and a plurality of emitter leads of the emitter are electrically connected to the emitter contact portion. Additional steps are forming a connector at the connector end configured to electrically communicate with a patient cable and mounting the substrate to a retainer configured so that the substrate can be attached to living tissue. In one embodiment the attaching step comprises the substep of crimping the detector leads and the emitter leads onto the detector contact portion and the emitter contact portion, respectively.

In one embodiment, the forming step comprises the substeps of stripping a third portion of insulation from the connector end to expose a connector contact portion of the conductors, disposing a plurality of pins around the connector contact portion, and encapsulating the pins to form a connector housing. In an alternative embodiment, a substep is welding a connector shell around the pins to form a connector housing. The connector contact portion is in electrical communication with the detector contact portion and the emitter contact portion. Another embodiment comprises the further steps of removing an insulation window between the connector end and the component end to expose an ID element contact portion of the conductors, and attaching an ID element within the window so that a plurality of ID element leads of the ID element are electrically connected to the ID element contact portion. Yet another embodiment comprises the further steps of exposing a detector shield conductor at the component end, where the detector shield conductor is embedded within a conductive layer of the substrate extending from the component end to the connector end, attaching a shield to the detector, and electrically connecting the detector shield conductor to the detector shield.

Yet another aspect of a physiological sensor comprises an emitter means for transmitting light into tissue, a detector means for receiving light from tissue, a connector means for providing external instrument communication, a ribbon cable means for conducting electrical signals between the connector and each of the emitter and the detector, and a retainer means for attaching the ribbon cable means to tissue. In one embodiment, the physiological sensor further comprising a window means for attaching an ID element to the ribbon cable means. In another embodiment, the physiological sensor further comprises a first shielding means disposed within the ribbon cable means for suppressing electrical noise at the detector. A second shielding means may also be disposed within the ribbon cable means and around the first shielding means for suppressing electrical noise.

BRIEF DESCRIPTION OF THE DRAWINGS

FIGS. 4–11 are perspective views of assembly steps for a ribbon cable sensor;

FIG. 4 is a perspective view of an uncut portion of ribbon cable;

FIG. 5 is a perspective view of a ribbon cable cut to length to create a sensor substrate, with the insulation stripped at a connector end of the substrate to form connector contacts;

FIG. 6 is a perspective view of a ribbon cable substrate with insulation stripped at a component end of the substrate to form detector contacts;

FIG. 7 is a perspective view of a ribbon cable substrate with wires cut and insulation stripped at the component end of the substrate to form emitter contacts;

FIG. 8 is a perspective view of a ribbon cable substrate with an insulation window cut between the connector and component ends along the LED wires to form ID element contacts;

FIG. 9B is a perspective view of an alternative component attachment utilizing crimp pins.

FIG. 10 is a perspective view of a ribbon cable substrate showing pin attachment at the connector end; and FIG. 11 is a perspective view of a ribbon cable substrate showing pin encapsulation at the connector end to form a patient cable connector;

DETAILED DESCRIPTION OF THE PREFERRED EMBODIMENT

Ribbon Cable Sensor Assembly

Figure 1:
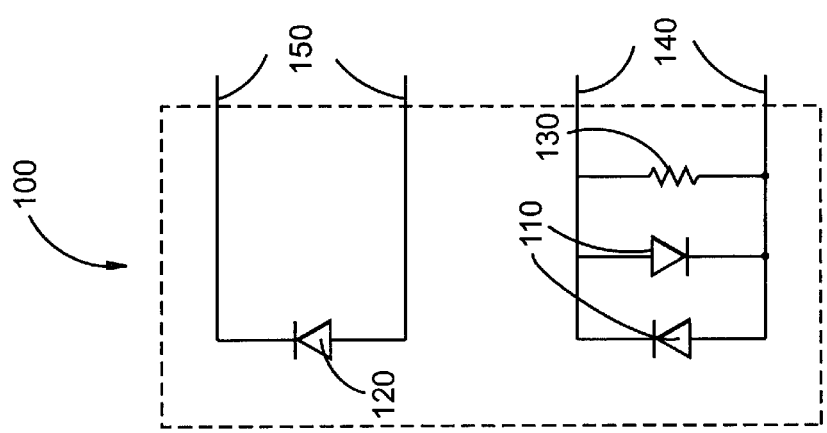
FIG. 1 is a schematic of a prior art sensor circuit.
Figure 2:
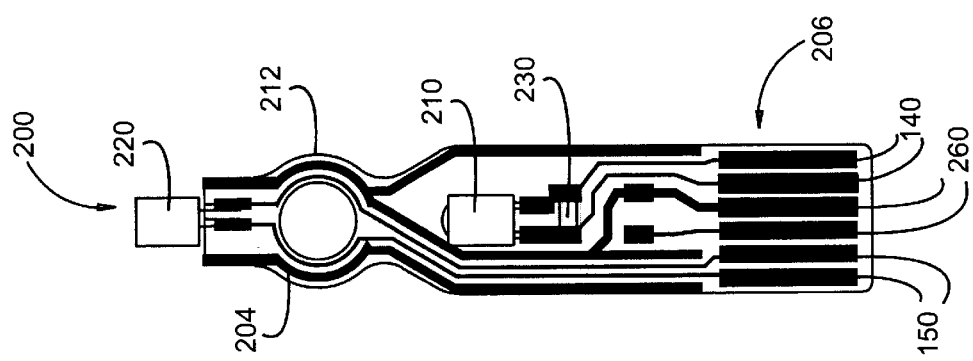
FIG. 2 is a trace-side view of a prior art flexible circuit substrate.
Figure 3:
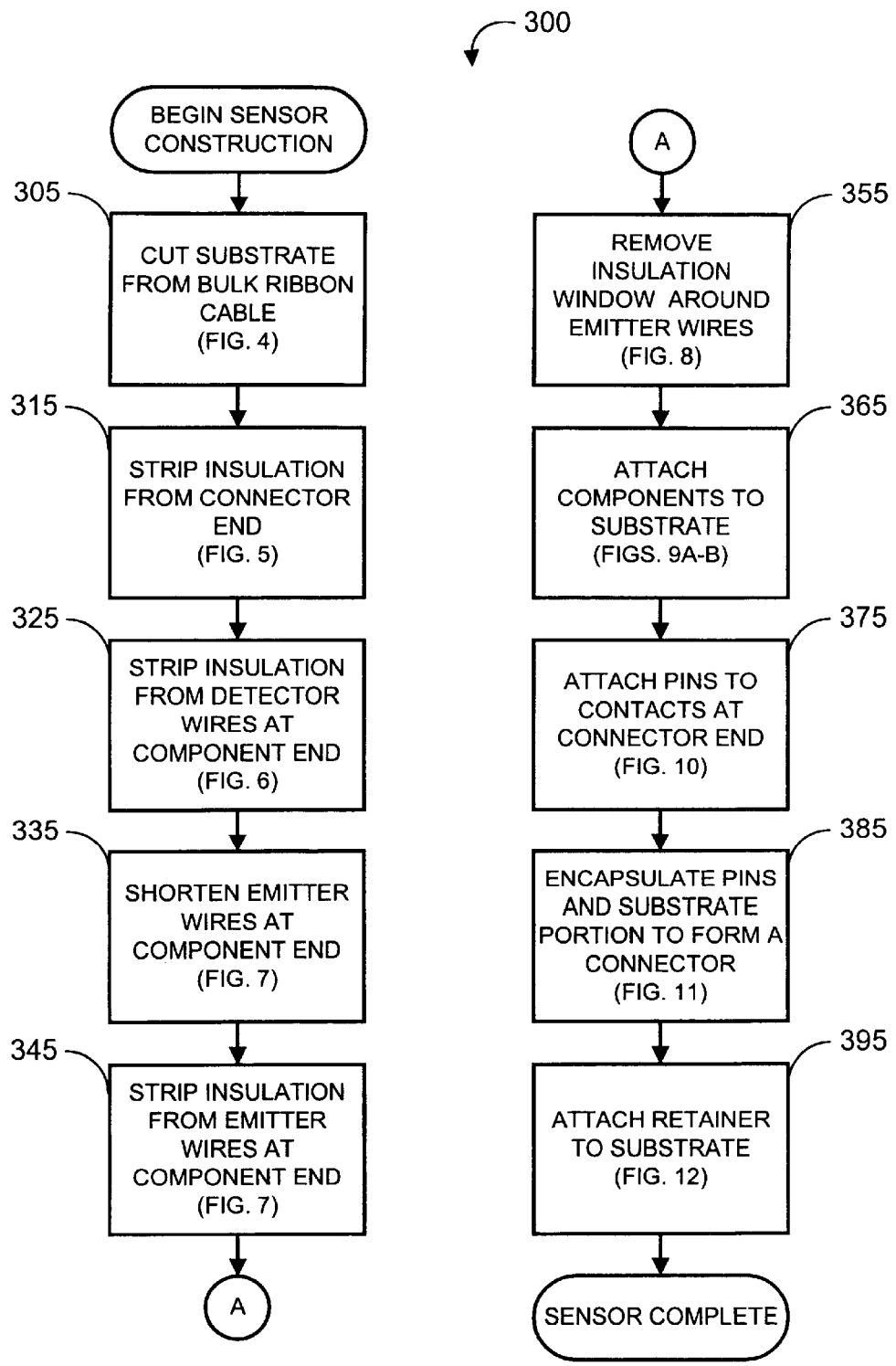
FIG. 3 is a flowchart of assembly steps for a ribbon cable sensor.
Figure 13:
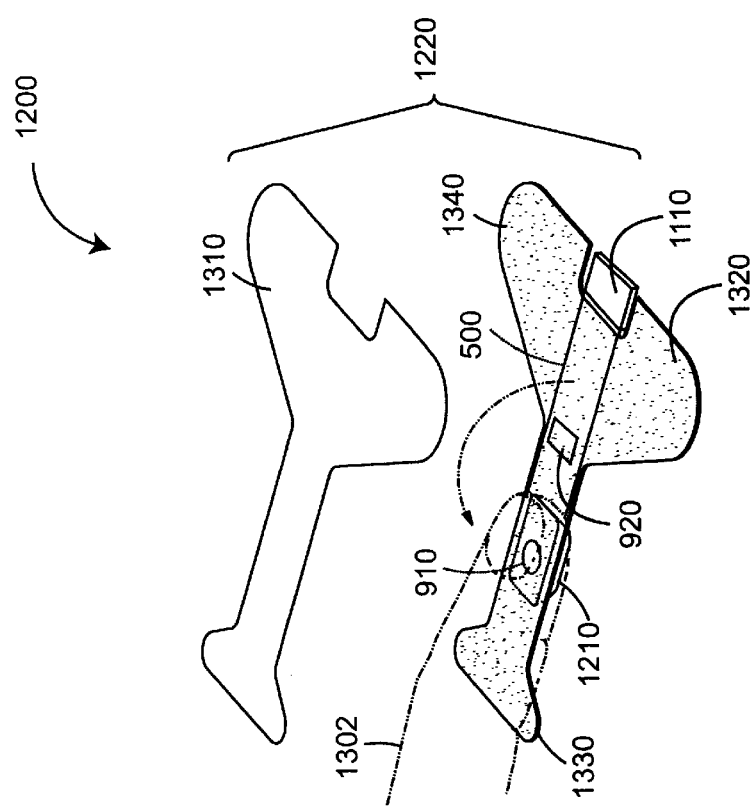
FIG. 13 is a perspective view of a ribbon cable substrate pulse oximetry sensor with adhesive backing removed in preparation for finger attachment.
Figure 14:
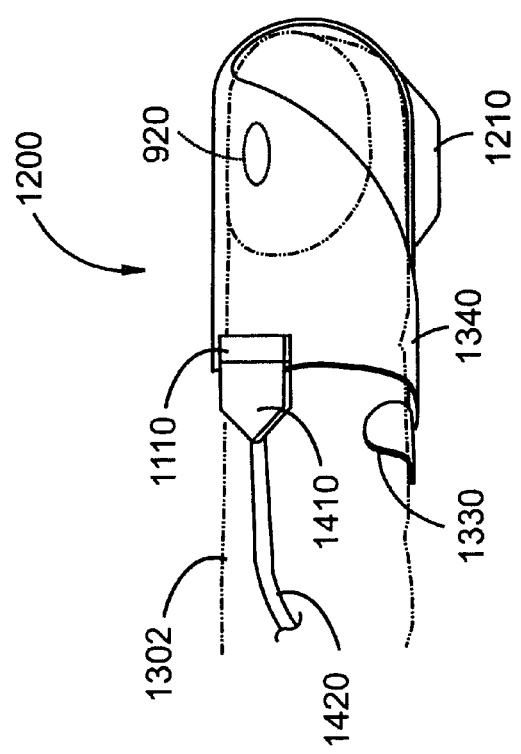
FIG. 14 is a perspective view of a ribbon cable substrate pulse oximetry sensor attached to a finger.
Figure 15:
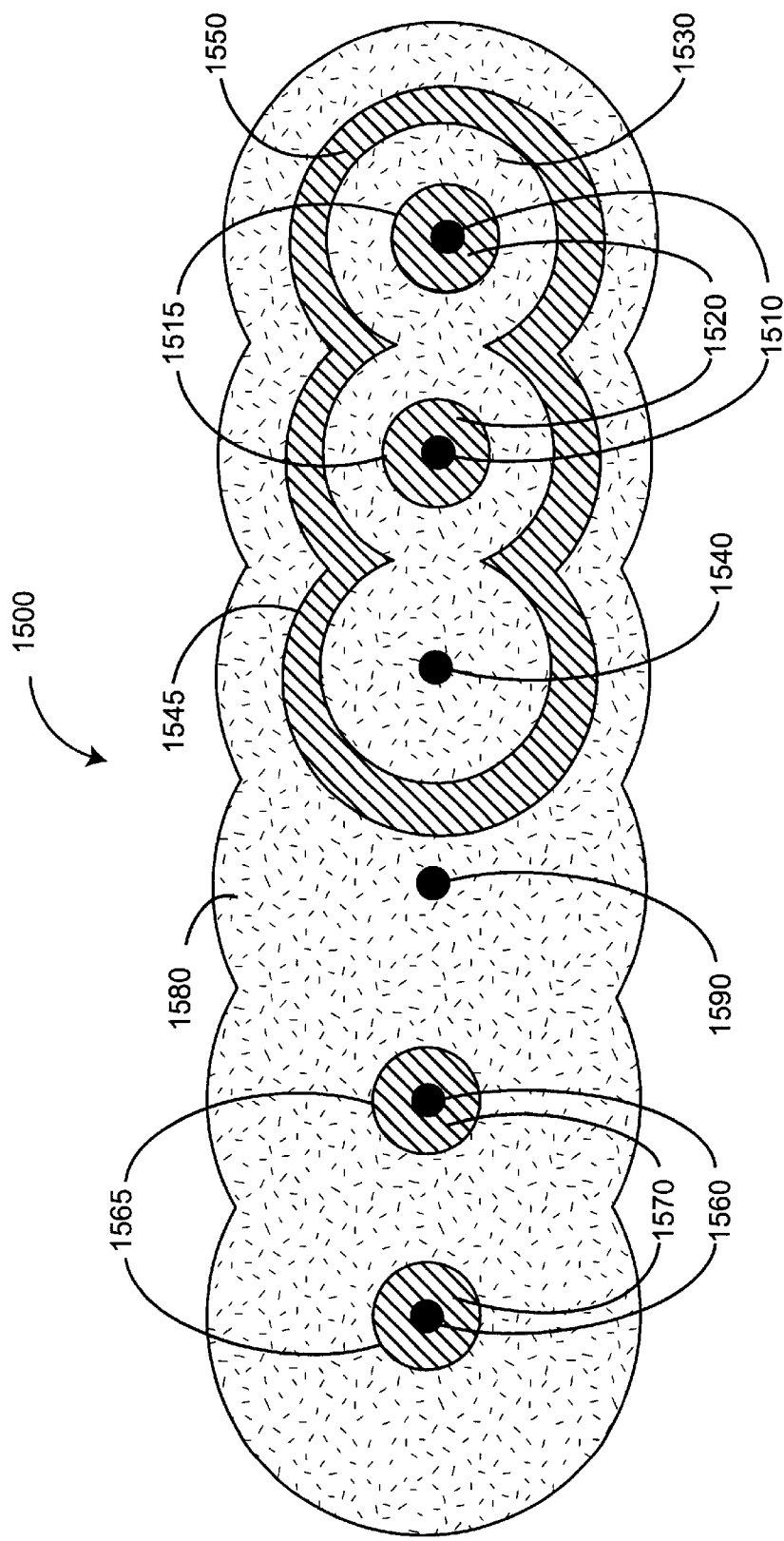
FIG. 15 is a cross-section view of an alternative ribbon cable substrate embodiment having conductive shield layers.

FIG. 3 describes assembly steps for one embodiment of a ribbon cable substrate pulse oximetry sensor ("ribbon cable sensor"). FIGS. 4–12 illustrate the assembly steps described in FIG. 3. FIGS. 13–14 illustrate finger attachment of an assembled ribbon cable sensor. FIG. 15 illustrates a ribbon cable having conductive layers and associated embedded conductors for constructing a shielded embodiment of a ribbon cable sensor, and FIG. 16 describes the assembly steps for a shielded embodiment of a ribbon cable sensor.

Figure 4:
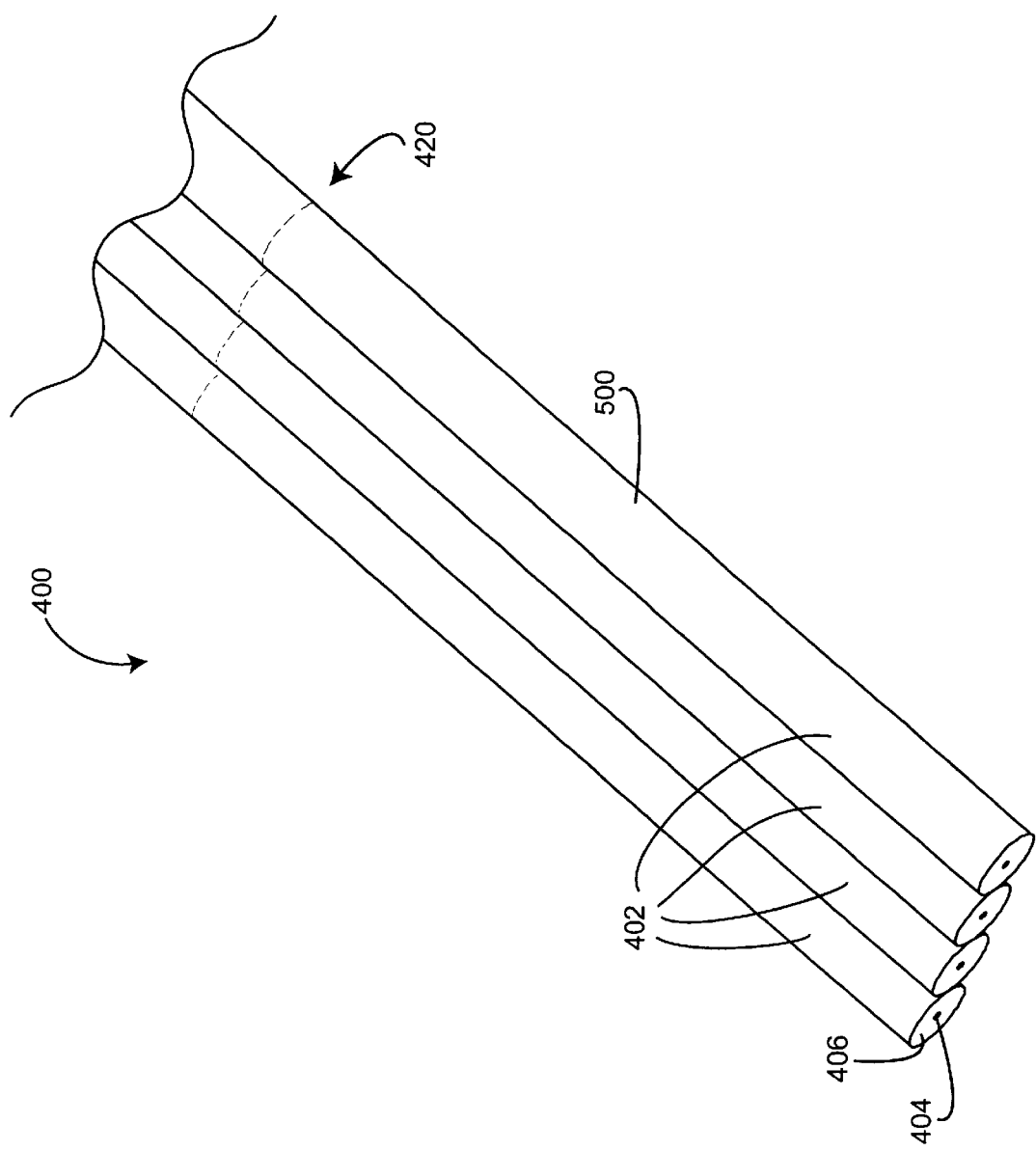

FIG. 4 illustrates that a ribbon cable substrate is initially cut from bulk ribbon cable 305 (FIG. 3). As shown in FIG. 4, one form of ribbon cable 400 has multiple wires 402, which are attached in a row lengthwise, as is well-known in the art. Each wire 402 has a conductor 404 that is surrounded by insulation 406. A substrate portion 500 can be detached from a bulk quantity of ribbon cable 400 by making a perpendicular cut 420 across the wires 402. For example, a length of ribbon cable corresponding to a particular sensor type, such as a neonatal, pediatric or adult sensor can be cut from one end of a bulk spool of ribbon cable. Advantageously, small quantities of custom-length sensors can be economically manufactured in this manner, which is not otherwise feasible with a flexible circuit sensor substrate. Also, the ribbon cable substrate is particularly suited to automated fabrication processes, as described below, further increasing the feasibility of small-quantity or custom sensor fabrication.

Figure 5:
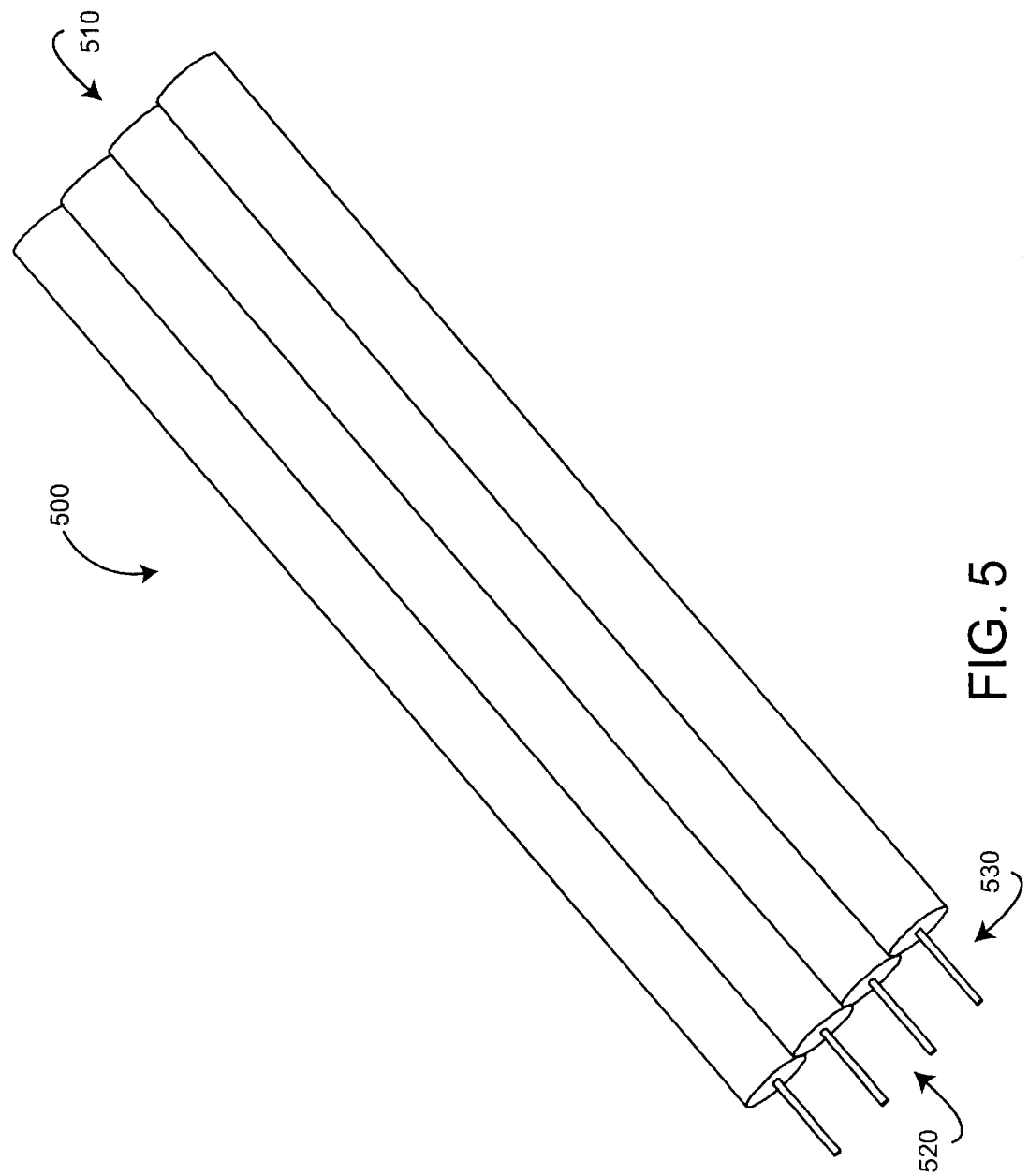

FIG. 5 illustrates that insulation is stripped at a connector end of the ribbon cable substrate 315 (FIG. 3). As shown in FIG. 5, a ribbon cable substrate 500 has a component end 510 and a connector end 520. Insulation is removed from an end portion of the wires 402 (FIG. 4) at the connector end 520, exposing connector contacts 530.

Figure 6:
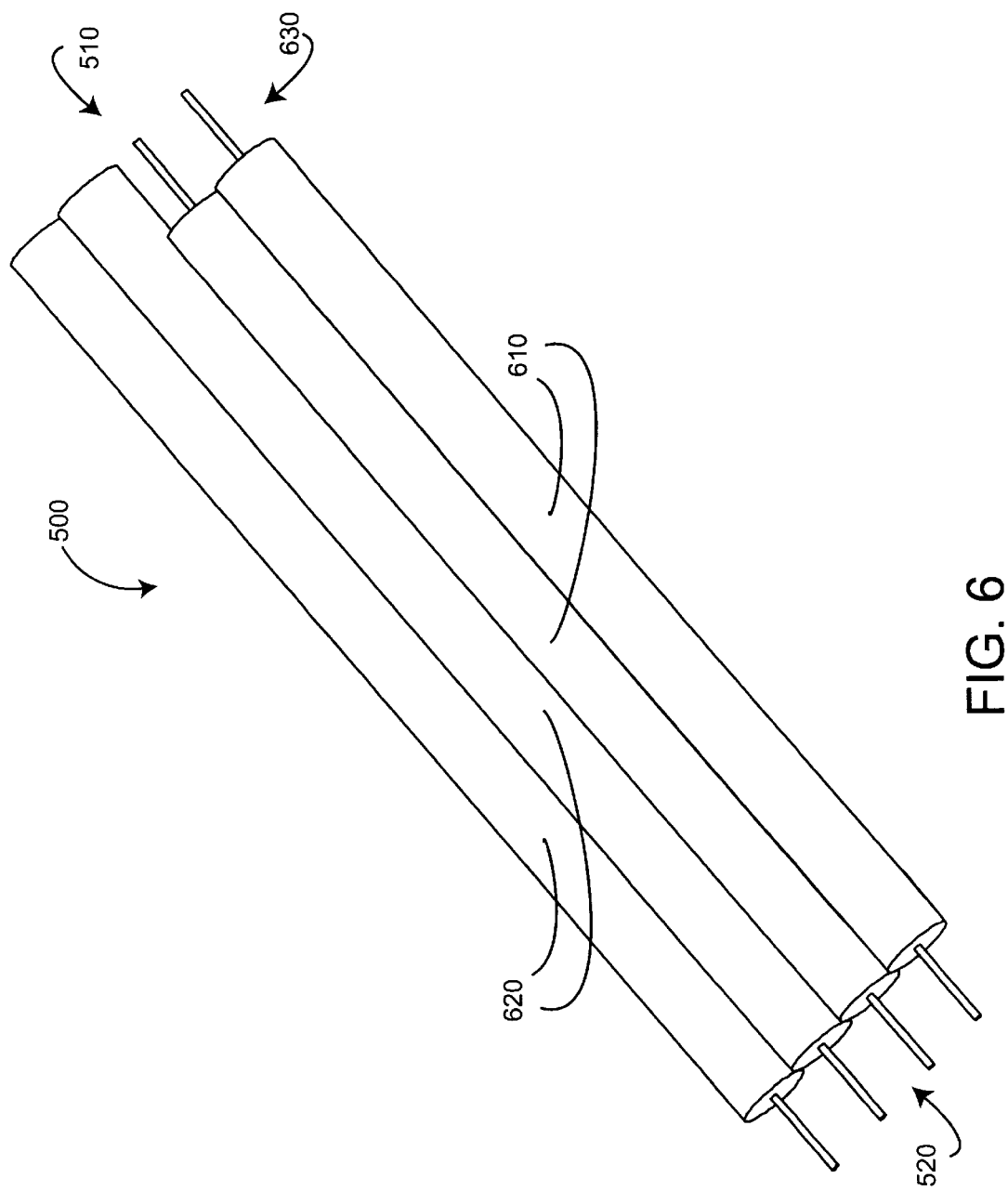

FIG. 6 illustrates that insulation is also stripped from detector wires at the component end of the ribbon cable substrate 325 (FIG. 3). As shown in FIG. 6, the substrate 500 has detector wires 610 and emitter wires 620. Insulation is removed from an end portion of the detector wires 610 at the component end 510, exposing detector contacts 630.

Figure 7:
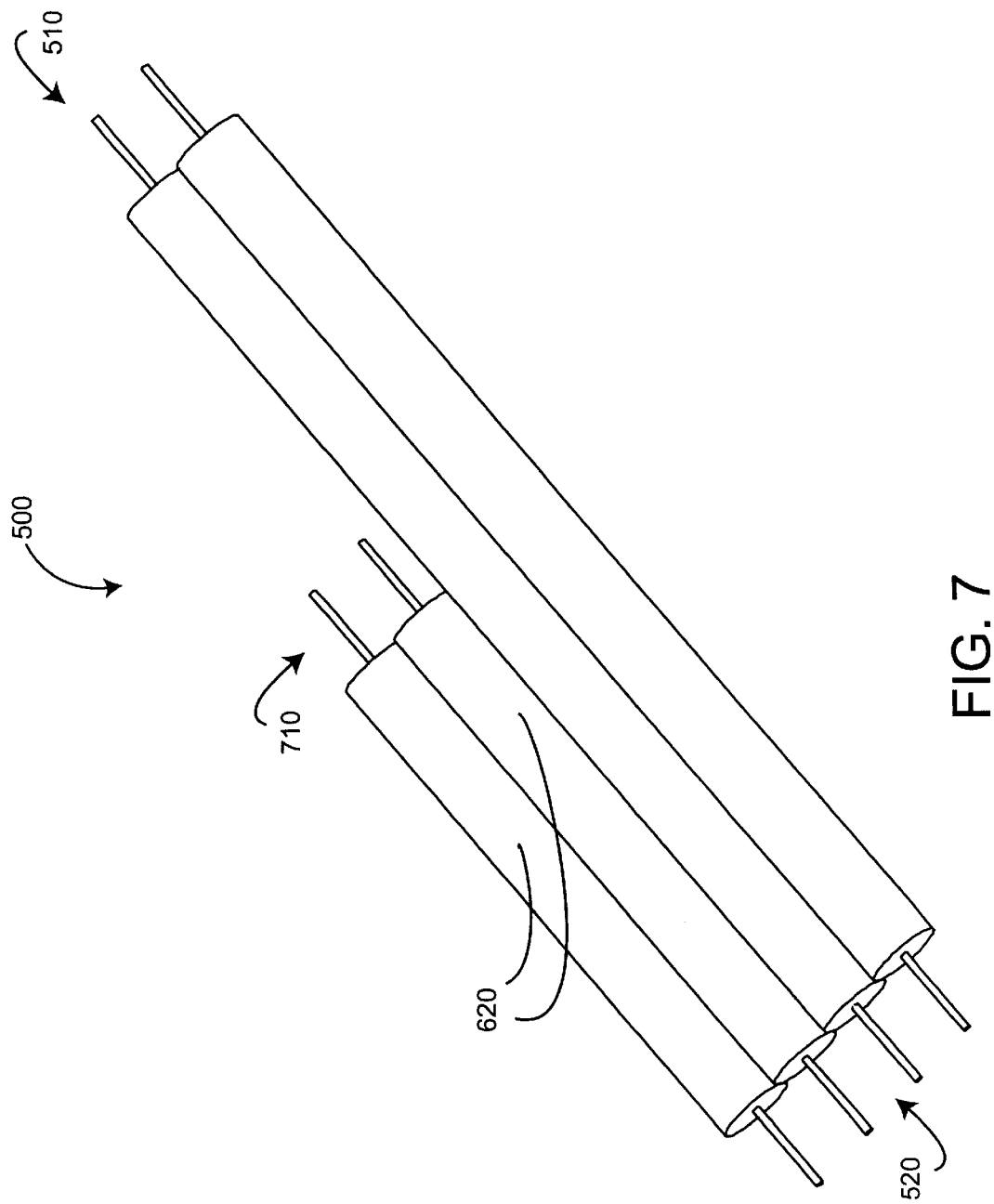

FIG. 7 illustrates that emitter wires are shortened at the component end of the ribbon cable substrate 335 (FIG. 3), and insulation is also removed from these emitter wires at the component end of the substrate 345 (FIG. 3). As shown in FIG. 7, the emitter wires 620 are cut back from the component end 510 to shorten their length. This allows the detector and emitter components of the sensor to be configured for tissue placement, such as on either side of a patient's fingertip, as described with respect to FIGS. 13–14, below. Insulation is then removed from an end portion of the emitter wires 620 at the component end 510, exposing emitter contacts 710.

Figure 8:
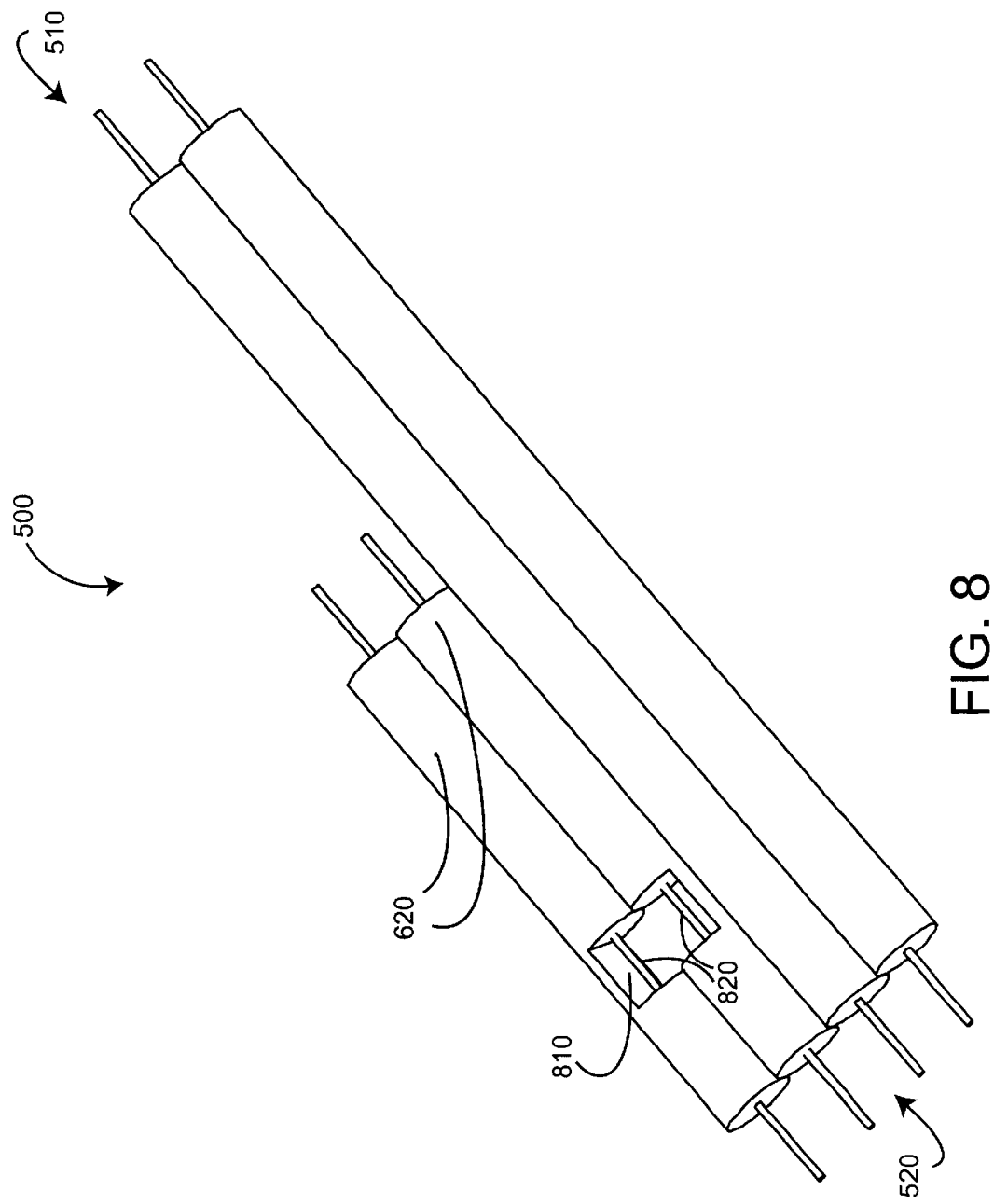

FIG. 8 illustrates that insulation is removed from a window around the emitter wires 355 (FIG. 3). As shown in FIG. 8, a punch or similar apparatus is used to remove a window 810 of insulation around the emitter wires 620 between the component end 510 and the connector end 520, exposing ID element contacts 820. At this stage of assembly, the ribbon cable substrate 500 is ready for component attachment.

Figure 9A:
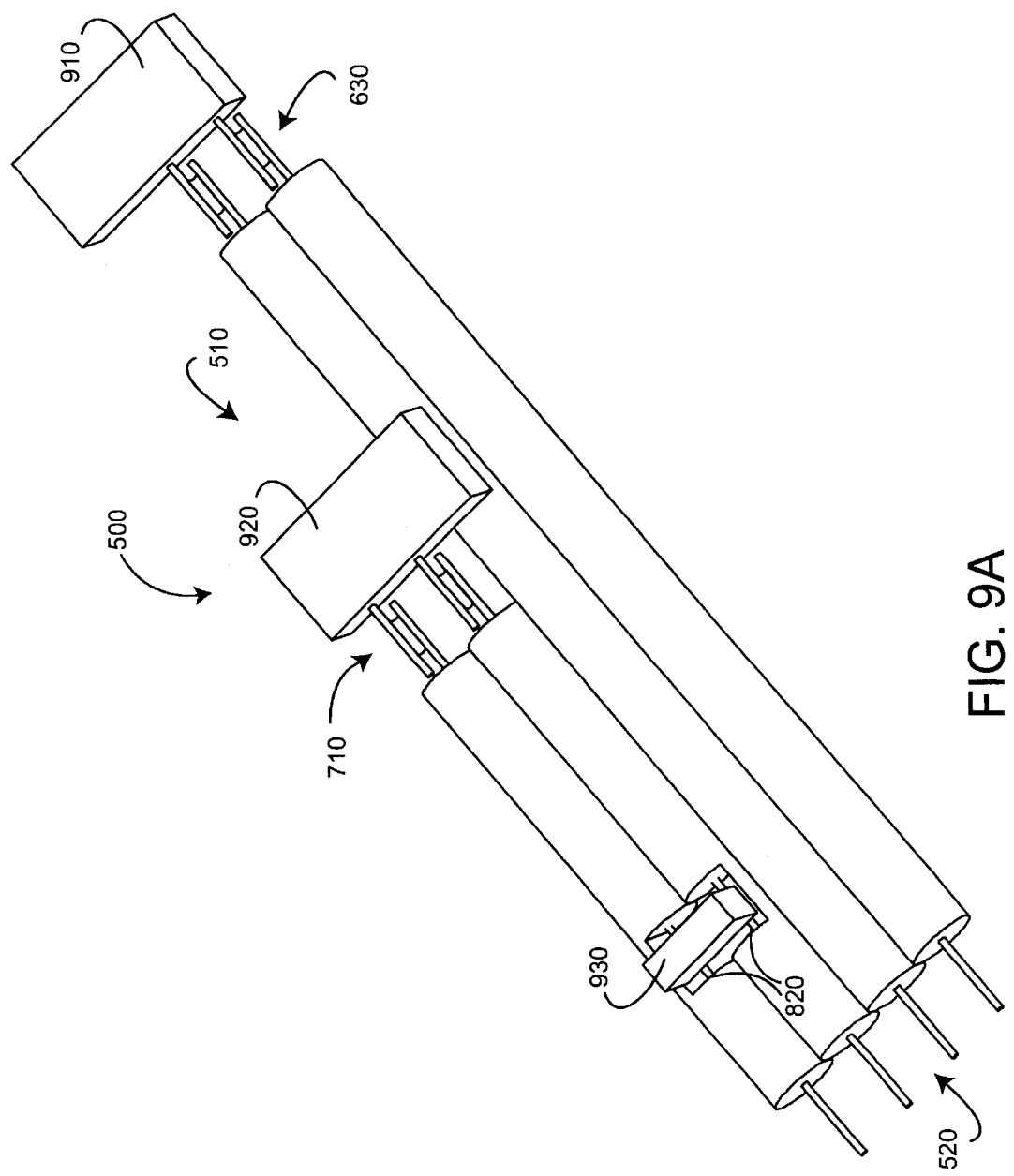
FIG. 9A is a perspective view of a ribbon cable substrate showing soldered component attachment.

FIG. 9A illustrates that components are attached to the substrate 365 (FIG. 3). As shown in FIG. 9, a detector 910 is attached to the detector contacts 630 at the component end 510 of the ribbon cable substrate 500. The detector 910 is typically a photodiode mounted on a leaded carrier and encapsulated. The detector leads can be soldered, for example, to the detector contacts 630 by hand or by an automated process, such as wave solder. One of ordinary skill in the art will recognize other techniques of accomplishing an electrical and mechanical connection between the detector 910 and the detector contacts 630, such as spot welding. Likewise, an emitter 920 is attached to the emitter contacts 710, also at the component end 510 of the substrate 500. The emitter 920 typically has both a red LED (light emitting diode) and an IR (infrared) LED mounted on a common leaded carrier and encapsulated. In a similar fashion, an ID element 930, such as a leadless resistor, is attached to the ID element contacts 820.

FIG. 9B illustrates an alternative component attachment to the ribbon cable substrate using crimp pin components. In this embodiment, a detector 910 has crimp pin leads 912 that accept the detector contacts 630 of the ribbon cable substrate 500. A crimping tool is used to mechanically and electrically attach the detector leads 912 to the wires of the detector contacts 630, as is well known in the art. Similarly, an emitter 920 has crimp pin leads 922 that accept and attach to the emitter contacts 710 with the use of a crimping tool. Leads of an ID element (not shown) can also be placed adjacent the wires of the emitter contacts 710 inside the emitter crimp pin leads 922, and, using a crimping tool, the ID element, emitter 920 and emitter contacts 710 can be attached together.

Figure 10:
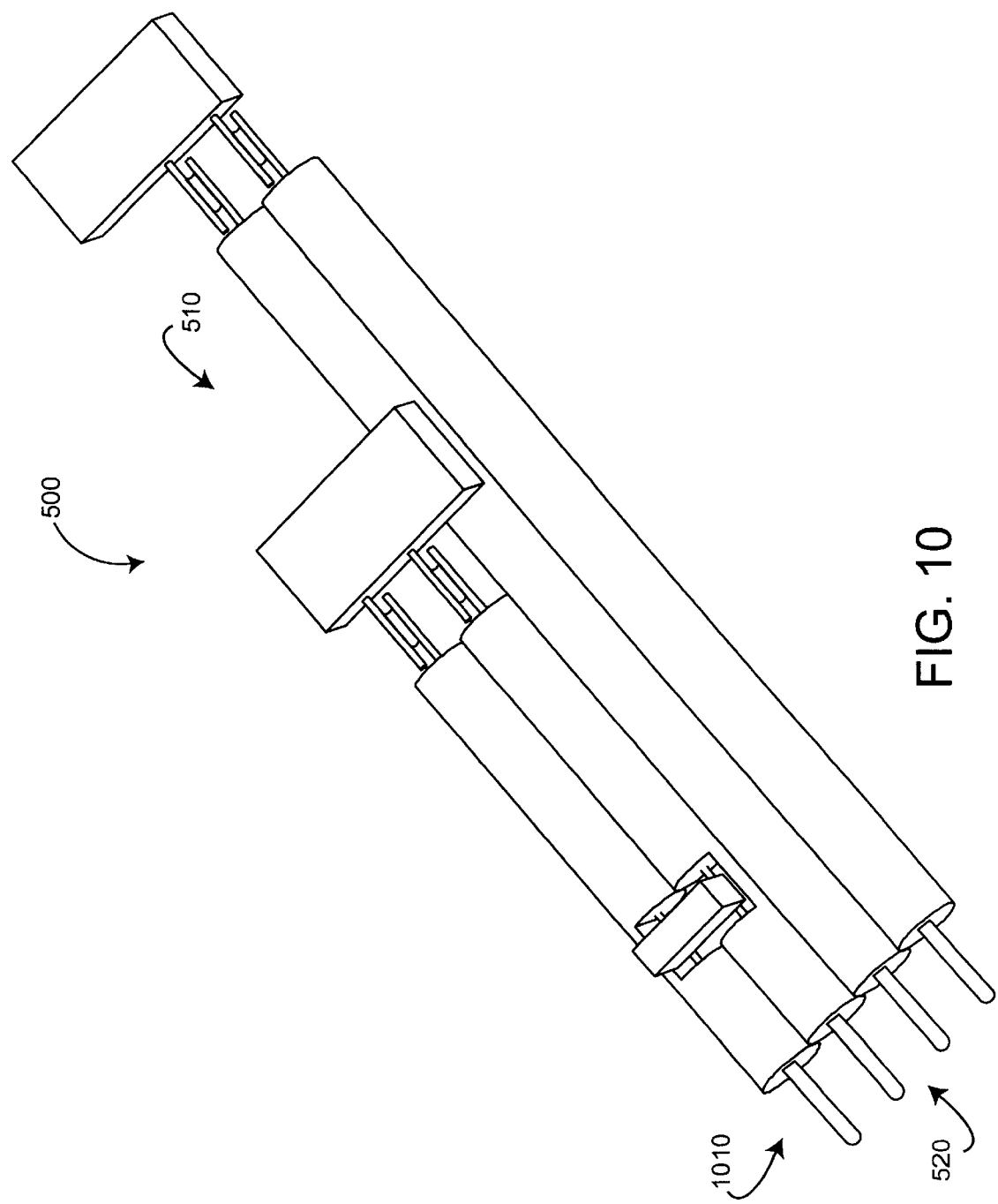

FIG. 10 illustrates that connector pins are attached to the connector contacts 375 (FIG. 3). As shown in FIG. 10, individual pins 1010 are mounted over and attached to the connector contacts 530 (FIG. 5), using a reflow solder technique, for example. Alternatively, the connector pins 1010 can be crimp pins that are attached to the wires of the connector contacts 530 (FIG. 5) using a crimping tool. Advantageously, construction of a ribbon cable substrate pulse oximetry sensor can be significantly automated if crimp pin component attachment (FIG. 9B) and crimp pin connector pin attachment are used.

Figure 11:
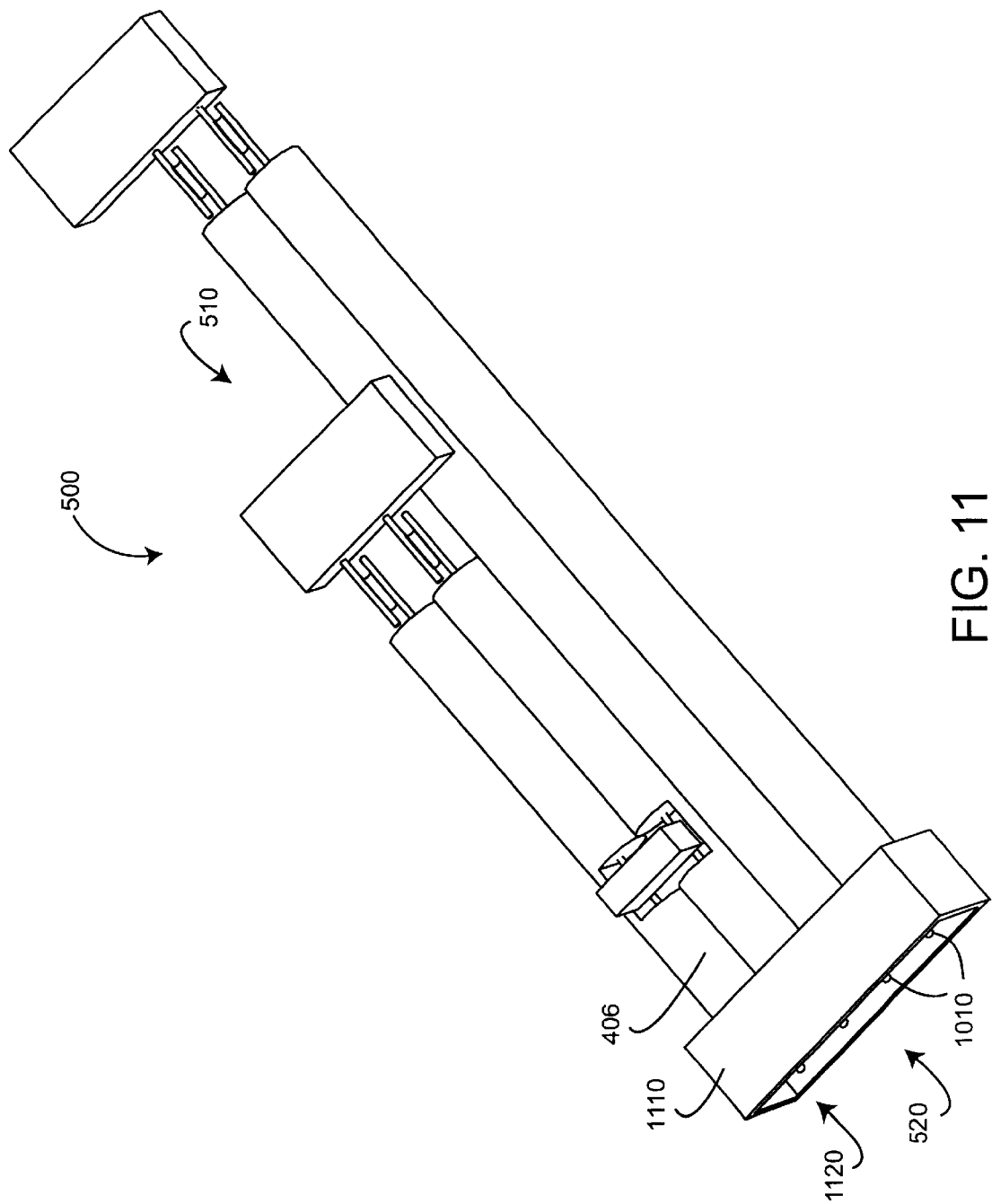

FIG. 11 illustrates that the connector pins and portions of the substrate are encapsulated to form a connector 385 (FIG. 3). As shown in FIG. 11, a connector 1110 is constructed at the connector end 520 of the ribbon cable substrate 500 so that the pins 1010 can be accessed through a connector opening 1120. In one embodiment, the connector 1110 is created by molding an encapsulant around the pins 1010 and a portion of the insulation 406 adjoining the pins. In another embodiment, the connector 1110 is created by ultrasonic welding two halves of a connector shell that is clamped over the pins 1010 and a portion of the insulation 406 adjoining the pins 1010. Completion of the ribbon cable substrate 500 may involve further steps (not shown) such as shielding the detector, installing the detector within a cavity 1210 (FIG. 12), and applying a protective layer over the substrate and associated components.

Figure 12:
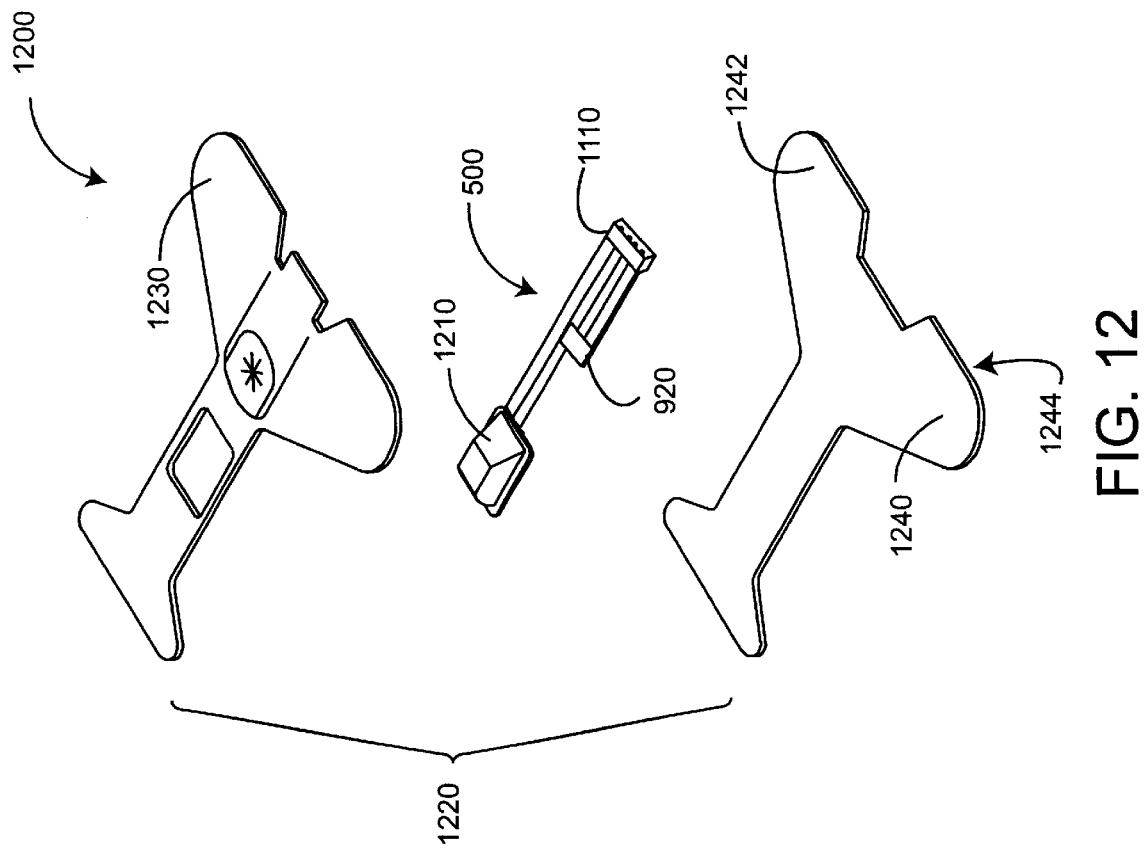
FIG. 12 is an exploded view of tape layers attached to a ribbon cable substrate to create an assembled pulse oximetry sensor.

FIG. 12 illustrates that a retainer is attached to the completed substrate 395 (FIG. 3). As shown in FIG. 12, a complete ribbon cable substrate pulse oximetry sensor 1200 is formed by attaching a retainer 1220 to the ribbon cable substrate 500, where the retainer 1220 functions to removably hold the sensor 1200 to a tissue sample, as described with respect to FIGS. 13–14, below. In this embodiment, the substrate 500 has a detector cavity 1210 containing a detector (not shown), an emitter 920 and a patient cable connector 1110. The retainer 1220 has a face tape layer 1230, similar to bandage strip material, and a clear base tape layer 1240 that allows red and IR light transmission. The base tape layer 1240 has exposed adhesive on one side 1242 that secures the face tape layer 1230 and an adhesive covered with a removable backing material 1310 (FIG. 13) on another side 1244 that secures the sensor 1200 and integrated substrate 500 to a tissue sample. The face tape layer 1230 and base tape layer 1240 are configured to accommodate the connector 1110 and the detector cavity 1210.

Ribbon Cable Sensor Attachment

FIG. 13 illustrates a ribbon cable substrate pulse oximetry sensor 1200 in preparation for finger attachment. Backing 1310 is removed from the retainer 1220 exposing an adhesive 1320. A finger 1302 is placed along the substrate 500 against the adhesive 1320 as shown, so that the detector 910 is positioned directly underneath the fingertip. The substrate 500 can then be folded over the fingertip so that the emitter 920 is positioned directly above the fingertip. In this manner, the red and IR LEDs in the emitter 920 can transmit light through the fingernail bed, which is received by the detector 910 on the other side of the finger 1302. In this embodiment, a small pair of flaps 1330 and a large pair of flaps 1340 wrap around the finger 1302 to securely retain the substrate 500 to the finger tissue, as shown in FIG. 14.

FIG. 14 illustrates a ribbon cable substrate pulse oximetry sensor 1200 attached to a tissue sample. When attached, the detector cavity 1210 containing the detector 910 (FIG. 13) is positioned under the fingertip and the emitter 920 is positioned over the fingernail, as described with respect to FIG. 13, above. The flaps 1330, 1340 are wrapped around the finger 1302, also as described above. The connector 1110 is attached to a patient cable 1420 via a mating patient cable connector 1410. In this manner, the patient cable transmits electrical signals between the detector 910 (FIG. 13), the emitter 920, the ID element 930 (FIG. 9) and an external pulse oximetry monitor (not shown).

Shielded Ribbon Cable Sensor

FIG. 15 illustrates a cross-section of a shielded ribbon cable substrate 1500. In this embodiment, the substrate 1500 has six conductors as compared to the four conductors 404 (FIG. 4) in the ribbon cable embodiment described above. The shielded ribbon cable substrate 1500 has two detector conductors 1510, which are each surrounded by a detector conductor insulation layer 1520 to form a detector wire structure 1515. The detector wire structure 1515 serves a similar function as the detector wires 610 (FIG. 6) described above. The detector wire structure 1515 is, in turn, embedded within a conductive detector shield layer 1530. A detector shield conductor 1540 is embedded in the detector shield layer 1530, allowing external connection to that layer. The detector shield layer 1530 is embedded within a shield insulation layer 1550 to form a shielded detector cable structure 1545.

The shielded ribbon cable substrate 1500 also has two emitter conductors 1560, which are each surrounded by an emitter conductor insulation layer 1570 to form an emitter wire structure 1565. The emitter wire structure 1565 serves a similar function as the emitter wires 620 (FIG. 6) described above. The emitter wire structure 1565 and the shielded detector cable structure 1545 are both embedded within a conductive substrate shield layer 1580. A substrate shield conductor 1590 is embedded in the conductive substrate shield layer 1580, allowing external connection to that layer. The entire substrate 1500 may be covered in an additional insulation layer (not shown). The conductive layers 1530, 1580 may be, for example, a conductive polymeric material.

Figure 16:
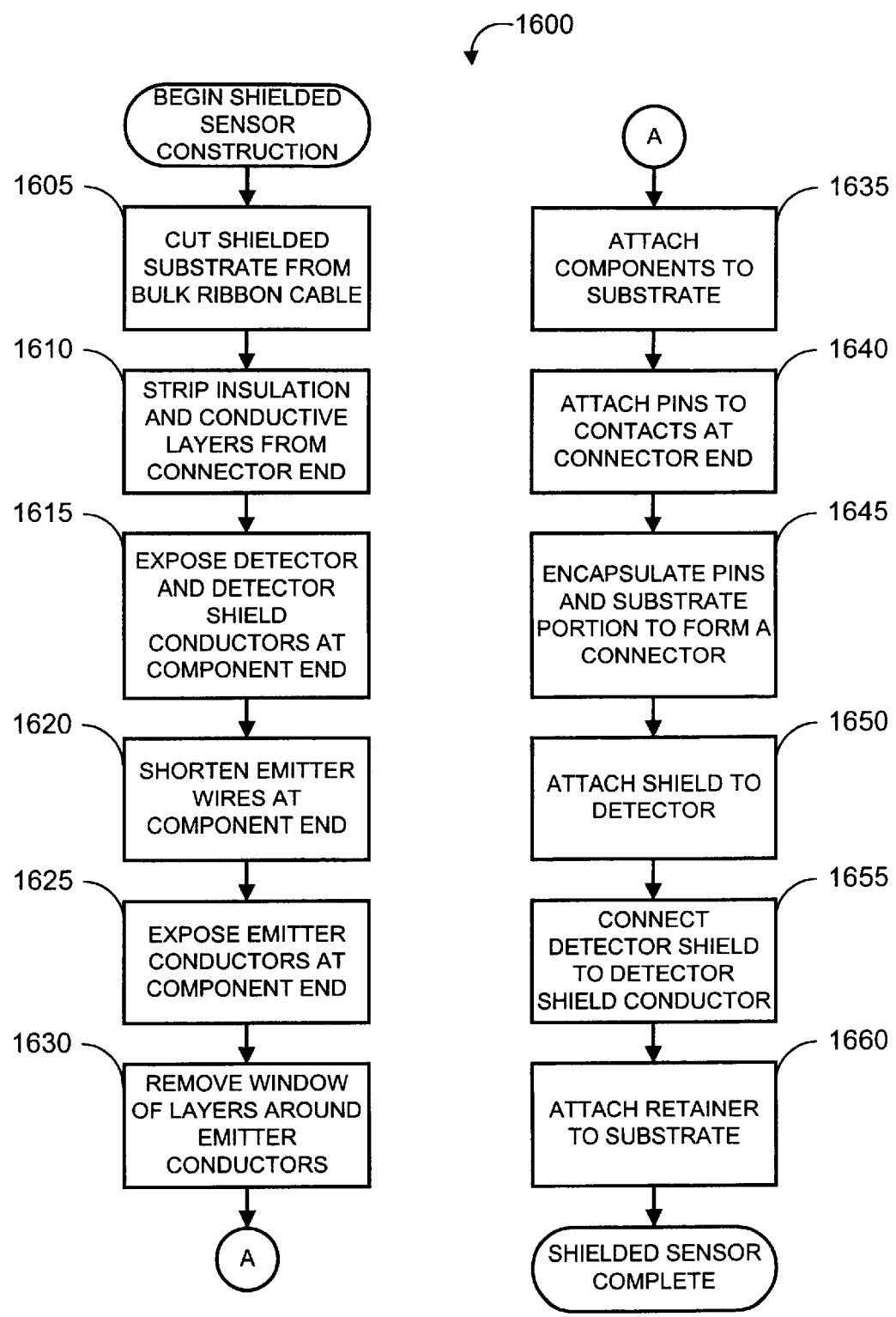
FIG. 16 is a flowchart of the assembly steps for a shielded ribbon cable sensor.

FIG. 16 illustrates the assembly steps for a shielded ribbon cable sensor. As shown, a shielded ribbon cable substrate is initially cut from bulk ribbon cable 1605. Insulation and conductive layers are stripped at a connector end of the ribbon cable substrate to expose the conductors and create connector contacts 1610. These connector contacts include portions of the detector conductors 1510 (FIG. 15), the emitter conductors 1560 (FIG. 15) and the shield conductors 1540, 1590 (FIG. 15). Further, insulation and conductive layers are stripped at the component end of the ribbon cable substrate to expose the detector and detector shield conductors 1615. The emitter wires are shortened at the component end of the substrate 1620, and insulation and conductive layers are removed to expose the emitter conductors at the component end 1625. Also, insulation and conductive layers are removed from a window around the emitter conductors between the component and connector ends of the substrate 1630. Components are attached to the substrate 1635, and connector pins are attached to the connector contacts 1640. The connector pins and portions of the substrate at the connector end are encapsulated to form a connector 1645. Alternatively, two halves of a connector shell are clamped around the connector pins and portions of the substrate at the connector end and ultrasonically welded. A shield is attached to the detector component 1650, and the detector shield is connected to the detector shield conductor 1655. A retainer is attached to the substrate to form a shielded sensor 1660. Completion of the shielded ribbon cable sensor may involve further steps (not shown) such as installing the detector within a cavity 1210 (FIG. 12), and applying a protective layer over the substrate and associated components.

A ribbon cable substrate pulse oximetry sensor has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological sensor comprising:

a ribbon cable having a plurality of conductors extending within an insulation layer between a first end and a second end;

a detector mounted to ones of said plurality of conductors of said ribbon cable, thereby electrically connecting to at least a first pair of said conductors;

an emitter mounted to others of said plurality of conductors of said ribbon cable and electrically connected to at least a second pair of said conductors, at least one of said detector and said emitter being mounted proximate said first end;

a connector mounted to said ribbon cable proximate said second end; and a retainer mounted to said ribbon cable and configured to removably attach said ribbon cable to tissue so that said emitter may transmit light into a tissue sample and said detector may receive light from said tissue sample.

2. The physiological sensor according to claim 1 wherein said detector is mounted to said ribbon cable proximate said first end and said emitter is mounted to said ribbon cable between said first and second ends, said ribbon cable being foldable around a tissue portion of a patient so that said emitter opposes said detector on either side of said tissue portion.

3. The physiological sensor according to claim 1 wherein said connector comprises:

a plurality of pins provided to said second end of said conductors, said insulation being stripped from the end portions at said second end; and an encapsulant disposed around a portion of said pins and said second end so as to form a housing portion of said connector.

4. The physiological sensor according to claim 1 wherein said connector comprises:

a plurality of pins provided to said second end portions of said conductors, said insulation being stripped from the end portions at said second end; and a welded connector shell disposed around a portion of said pins and said second end so as to form a housing portion of said connector.

5. The physiological sensor according to claim 1 wherein said ribbon cable comprises a first conductive layer shielding said first pair of conductors, said first conductive layer having a first embedded conductor extending to said connector.

6. The physiological sensor according to claim 5 further comprising a detector shield disposed around said detector and electrically connected to said first embedded conductor.

7. The physiological sensor according to claim 6 further comprising a second conductive layer shielding said first pair and said second pair of conductors, said second conductive layer having a second embedded conductor extending to said connector.

8. A physiological sensor comprising:

an emitter means for transmitting light;

a detector means for receiving light attenuated by tissue;

a connector means for providing external instrument communication;

a ribbon cable means for conducting electrical signals between said connector and each of said emitter and said detector without the use of conductors on a flexible substrate; and a retainer means for attaching said ribbon cable means to tissue.

9. The physiological sensor according to claim 8 further comprising a window means for attaching an ID element to said ribbon cable means.

10. The physiological sensor according to claim 8 further comprising a first shielding means disposed within said ribbon cable means for suppressing electrical noise at said detector.

11. The physiological sensor according to claim 10 further comprising a second shielding means disposed within said ribbon cable means and around said first shielding means for suppressing electrical noise.

\* \* \* \* \*